United States Patent
Hinman et al.

(10) Patent No.: US 8,821,242 B2
(45) Date of Patent: Sep. 2, 2014

(54) SYSTEMS AND METHODS FOR ENHANCING COGNITION

(71) Applicant: Lumos Labs, Inc., San Francisco, CA (US)

(72) Inventors: Tyler Hinman, San Francisco, CA (US); Ben Katz, Averill Park, NY (US); Joseph L. Hardy, Richmond, CA (US); David Drescher, San Francisco, CA (US)

(73) Assignee: Lumos Labs, Inc., San Francisco, CA (US)

( * ) Notice: Subject to any disclaimer, the term of this patent is extended or adjusted under 35 U.S.C. 154(b) by 24 days.

(21) Appl. No.: 13/780,882

(22) Filed: Feb. 28, 2013

(65) Prior Publication Data

US 2014/0031116 A1    Jan. 30, 2014

Related U.S. Application Data

(60) Provisional application No. 61/675,725, filed on Jul. 25, 2012.

(51) Int. Cl.
*A63F 9/24* (2006.01)
*G09B 5/00* (2006.01)
*A63F 3/00* (2006.01)
*A63F 13/00* (2014.01)

(52) U.S. Cl.
CPC ....................................... *A63F 13/00* (2013.01)
USPC ................. 463/15; 273/236; 434/362; 463/9; 463/23

(58) Field of Classification Search
None
See application file for complete search history.

(56) References Cited

U.S. PATENT DOCUMENTS

| | | | |
|---|---|---|---|
| 5,573,245 A * | 11/1996 | Weiner et al. ............. | 273/153 R |
| 6,606,480 B1 * | 8/2003 | L'Allier et al. ............... | 434/362 |
| 7,540,615 B2 * | 6/2009 | Merzenich et al. .......... | 351/246 |
| 7,773,097 B2 | 8/2010 | Merzenich | |
| 2003/0008270 A1 | 1/2003 | Fleishman | |

(Continued)

FOREIGN PATENT DOCUMENTS

| | | |
|---|---|---|
| JP | 2002-222435 A | 8/2002 |
| KR | 10-2008-0013829 | 2/2008 |

(Continued)

OTHER PUBLICATIONS

Softschools.com, Path Memory, Nov. 4, 2011, http://www.softschools.com/games/memory_games/path_memory/.*

(Continued)

*Primary Examiner* — Dmitry Suhol
*Assistant Examiner* — Jason Yen
(74) *Attorney, Agent, or Firm* — Shartsis Friese LLP; Cecily Anne O'Regan; William C. Cray

(57) ABSTRACT

The disclosure is directed to cognitive training exercise adapted to train working memory systems in mammals in an intuitive, engaging, and adaptively challenging way to enhance cognition. Exercises engage users in the task of first seeing a grid with angled "bumpers" placed in various places throughout the grid. After a short initial presentation, the bumpers disappear, and the user must remember the location and orientation of the bumpers and calculate a route that a "pinball" will travel after being released from a designated starting position. In this way, the user is manipulating the remembered grid layout in working memory to solve a physically realistic task.

20 Claims, 15 Drawing Sheets

(56) References Cited

U.S. PATENT DOCUMENTS

| | | | |
|---|---|---|---|
| 2006/0003298 | A1 | 1/2006 | Greenspan et al. |
| 2007/0254270 | A1 | 11/2007 | Hearsh |
| 2007/0299802 | A1* | 12/2007 | Kwok .............................. 706/52 |
| 2008/0003553 | A1 | 1/2008 | Stark et al. |
| 2008/0084427 | A1 | 4/2008 | Delahunt et al. |
| 2011/0097697 | A1 | 4/2011 | Tharanathan et al. |
| 2012/0258436 | A1* | 10/2012 | Lee .............................. 434/362 |
| 2013/0101975 | A1 | 4/2013 | Hardy |

FOREIGN PATENT DOCUMENTS

| | | |
|---|---|---|
| KR | 10-2008-0067055 A | 7/2008 |
| KR | 10-2010-0051309 A | 5/2010 |
| KR | 10-2010-00867 B1 | 12/2010 |
| WO | WO 2009/015284 A2 | 4/2009 |
| WO | WO 2011/028422 A1 | 3/2011 |
| WO | WO 2013/043781 A2 | 3/2013 |
| WO | WO 2013/043781 A3 | 3/2013 |

OTHER PUBLICATIONS

Funny Games, Grid Memory, Aug. 21, 2011, http://www.funnygames.biz/grid-memory.html.*

Improvememory.org, Memory Games, Mar. 12, 2012, http://www.improvememory.org/games.*

Crone, Eveline A. Neurocognitive Development of Rational Reasoning. Developmental Science, Jan. 2009, vol. 12, Issue 1, pp. 55-56; See p. 2, lines 5-22, and figure 1.

Jaeggi, S. M., Buschkuehl, M., Jonides, J., & Perrig, W. J. (2008). Improving fluid intelligence with training on working memory. Proceedings of the National Academy of Sciences of the United States of America, 105(19), 6829-6833.

Kane, M., & Engle, R. (2002). The role of prefrontal cortex in working-memory capacity, executive attention, and general fluid intelligence: An individual-differences perspective. Psychonomic Bulletin & Review, 9(4), 637-671. doi:10.3758/BF03196323.

Daneman, M., & Carpenter, P. A. (1980). Individual differences in working memory and reading. Journal of Verbal Learning and Verbal Behavior, 19(4), 450-466. doi:10.1016/S0022-5371(80)90312-6.

Turner, M. L., & Engle, R. W. (1989). Is working memory capacity task dependent? Journal of Memory and Language, 28(2), 127-154. doi:10.1016/0749-596X(89)90040-5.

Levitt, H. (1971) Transformed Up-Down Methods in Psychoacoustics, J. Acoustical. Soc of Am., 49(2), 467-77.

Martzen, L., et al. (2010) Recreating Raven's Software for Systematically generating large numbers of Ravin-like matrix problems with normed properties. Behavior Research Methods, 42(2), 525-541.

Salthouse, TA et al. (1990) Age and Experience Effects in Spatial Visualization. Developmental Psychology 26(1) 128-136.

Ekstrom, RB, et al. (1976) Manual for Kit of Factor-Referenced Cognitive Tests, 173-179. Princeton NJ: Educational Testing Service.

Shepard, RN, et al. (1972) A Chronometric Study of Mental Paper Folding. Cognitive Psychology, 3(2), 228-243.

* cited by examiner

SYSTEMS AND METHODS FOR ENHANCING COGNITION

CROSS REFERENCE TO RELATED APPLICATIONS

This patent application claims the benefit of Provisional Patent Application Ser. No. 61/675,725, titled "Systems and Methods for Enhancing Cognition" filed on Jul. 25, 2012, the contents of which are incorporated herein by reference.

BACKGROUND OF THE INVENTION

Cognition is a group of mental processes that includes attention, memory, producing and understanding language, problem solving, and decision making Memory is the process by which information is encoded, stored and retrieved. Working memory is the ability to mentally operate on immediately available information while persisting this information for later potential encoding into long term memory. A considerable body of neuroscience research relates working memory capacity to other cognitive abilities such as fluid intelligence. Individuals with strong working memory capacities are more likely to succeed in education and professional environments. Enhancing this capacity is highly desirable.

There have been a number of attempts to develop programs to enhance working memory capacity. For example, Cogmed Inc. has developed several variants of working memory training aimed at enhancing cognition in children with a particular focus on reducing the burden of attention deficit hyperactivity disorder (ADHD). Jaeggi and colleagues have shown that training on a challenging working memory task—called the dual n-back—improves users' performance on measures of fluid intelligence. See, Jaeggi, S. M., Buschkuehl, M., Jonides, J., & Perrig, W. J. (2008). Improving fluid intelligence with training on working memory. *Proceedings of the National Academy of Sciences of the United States of America*, 105(19), 6829-6833. doi:10.1073/pnas.0801268105. These promising approaches demonstrate the appeal of working memory training; however, these approaches have limitations. In particular, most of these tasks do not require substantial mental manipulation of the to-be-remembered items. This can lead to reliance on domain-specific short term working memory systems, as opposed to the domain-general executive working memory systems. The operations of domain-general memory systems are associated with transfer of training to fluid intelligence and broadly to other kinds of tasks that require working memory and control of attention. See, Kane, M., & Engle, R. (2002). The role of prefrontal cortex in working-memory capacity, executive attention, and general fluid intelligence: An individual-differences perspective. *Psychonomic Bulletin & Review*, 9(4), 637-671. doi:10.3758/BF03196323. Exercising these systems in a targeted fashion requires mental manipulation of the items in memory, not just maintenance.

Researchers have used complex working memory tasks to measure and train the domain-general memory capacity. See, Daneman, M., & Carpenter, P. A. (1980). Individual differences in working memory and reading. *Journal of Verbal Learning and Verbal Behavior*, 19(4), 450-466. doi:10.1016/S0022-5371(80)90312-6; and Turner, M. L., & Engle, R. W. (1989). Is working memory capacity task dependent? *Journal of Memory and Language*, 28(2), 127-154. doi:10.1016/0749-596X(89)90040-5. However, these tasks typically involve separate items for retrieval and processing (e.g., solve a math problem while remembering an unrelated number or remembering the locations of objects in the order of the numbers printed on them). These designs lack ecological validity, in that most real world tasks involving memory and control of attention involve operating on the same items that are to be remembered. For example, when an individual is making a decision about the best way to travel from point A to point B, they must pull information into working memory such as the various possible routes, the impact of traffic, public transit delays, and if the routes are walkable and operate on those representations to decide on the optimal approach. Organic uses of complex working memory like this activate prefrontal cortex in a robust and ecologically relevant manner. These uses also have the advantage of being relatively easy tasks to understand, unlike the unnatural operations in most complex working memory tasks.

What is needed are cognitive training exercises that train working memory systems in an intuitive, engaging, and adaptively challenging way to enhance cognition.

SUMMARY OF THE INVENTION

Disclosed are cognitive training exercises that are adapted to train working memory systems in humans in an intuitive, engaging, and adaptively challenging way to enhance cognition. Exercises engage users in the task of first seeing a grid with angled "bumpers" placed in various places throughout the grid. After a short initial presentation, the bumpers disappear, and the user must remember the location and orientation of the bumpers and calculate a route that a "pinball" will travel after being released from a designated starting position. In this way, the user is manipulating the remembered grid layout in working memory to solve a physically realistic task.

In one aspect of the disclosure, methods for enhancing cognition of a participant are disclosed. A method for enhancing cognition in a participant, utilizing a computing device to present visual stimuli for training, and to record responses from the participant, the method comprising: providing multiple graphical elements in a board configuration, wherein the multiple graphical elements are available for visual presentation to the participant; visually presenting a temporal sequence of a plurality of the graphical elements, including displaying each graphical element at a respective location in a visual field, wherein the plurality of graphical elements includes two or more of each of one or more circular elements (e.g. pinballs), one or more linear elements (e.g., bumpers), and one or more decoy linear elements (e.g., decoy bumpers); requiring the participant to respond to the presented sequence, including indicating a travel path for the one or more circular elements from a start point to an end point which travel path involves the circular elements engaging the linear elements and not engaging the decoy linear elements; determining whether the participant responded correctly; modifying at least one of a duration of the visually presenting or complexity of the visually presenting (number of graphical elements) based on the determining; and repeating the visually presenting, the requiring, the determining and the modifying one or more times in an iterative manner to improve the cognition of the participant. Methods can also include displaying one or more of the graphical elements for a specified duration, then ceasing to display one or more of the graphical elements. Additionally, the board configuration can be in the form of a grid, and the size of the grid can be increased or decreased to provide an additional mechanism for increasing or decreasing the complexity of the program.

Another aspect of the disclosure provides a computer-readable memory medium that stores program instructions for enhancing cognition in a participant, utilizing a computing device to present visual stimuli for training, and to record responses from the participant, wherein the program instructions are executable by a processor. The readable memory is configurable to provide multiple graphical elements in a board configuration, wherein the multiple graphical elements are available for visual presentation to the participant; visually present a temporal sequence of a plurality of the graphical elements, including displaying each graphical element at a respective location in a visual field, wherein the plurality of graphical elements includes two or more of each of one or more circular elements (e.g. pinballs), one or more linear elements (e.g., bumpers), and one or more decoy linear elements (e.g., decoy bumpers); require the participant to respond to the presented sequence, including indicating a travel path for the one or more circular elements from a start point to an end point which travel path involves the circular elements engaging the linear elements and not engaging the decoy linear elements; determine whether the participant responded correctly; modify at least one of a duration of the visually presenting or complexity of the visually presenting (number of graphical elements) based on the determining; and repeat the visually presenting, the requiring, the determining and the modifying one or more times in an iterative manner to improve the cognition of the participant. Graphical elements can also be displayed for a specified duration, then ceasing to display one or more of the graphical elements. Additionally, the board configuration can be in the form of a grid, and the size of the grid can be increased or decreased to provide an additional mechanism for increasing or decreasing the complexity of the program.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE INVENTION

I. Computing Systems

The systems and methods described herein rely on a variety of computer systems, networks and/or digital devices, including mobile devices, for operation. In order to fully appreciate how the system operates an understanding of suitable computing systems is useful. The systems and methods disclosed herein are enabled as a result of application via a suitable computing system.

Figure 1A:
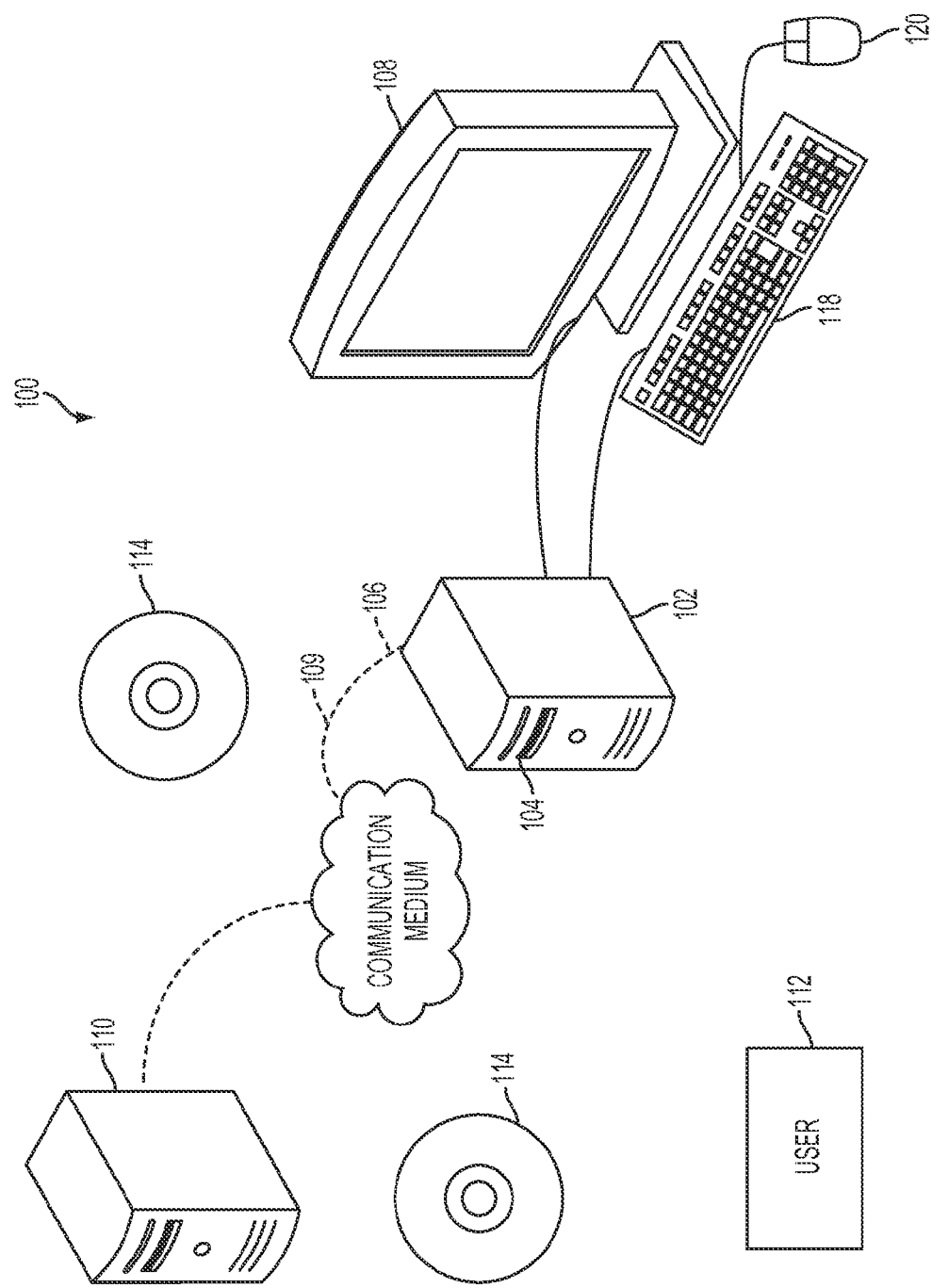
FIG. 1A is a block diagram showing a representative example of a logic device through which use of physically intuitive complex working memory tasks improve cognition in accordance with the disclosure.

FIG. 1A is a block diagram showing a representative example logic device through which a browser can be accessed to implement the present invention. A computer system (or digital device) 100, which may be understood as a logic apparatus capable of reading instructions from media 114 and/or network port 106, is connectable to a server 110, and has a fixed media 116. The computer system 100 can also be connected to the Internet or an intranet. The system includes central processing unit (CPU) 102, disk drives 104, optional input devices, illustrated as keyboard 118 and/or mouse 120 and optional monitor 108. Data communication can be achieved through, for example, communication medium 109 to a server 110 at a local or a remote location. The communication medium 109 can include any suitable means of transmitting and/or receiving data. For example, the communication medium can be a network connection, a wireless connection or an internet connection. It is envisioned that data relating to the present disclosure can be transmitted over such networks or connections. The computer system can be capable of, or in at least some situations capable of, communicating with a participant and/or a device used by a participant. The computer system is capable of communicating with other computers over the Internet, or with computers via a server.

Figure 1B:
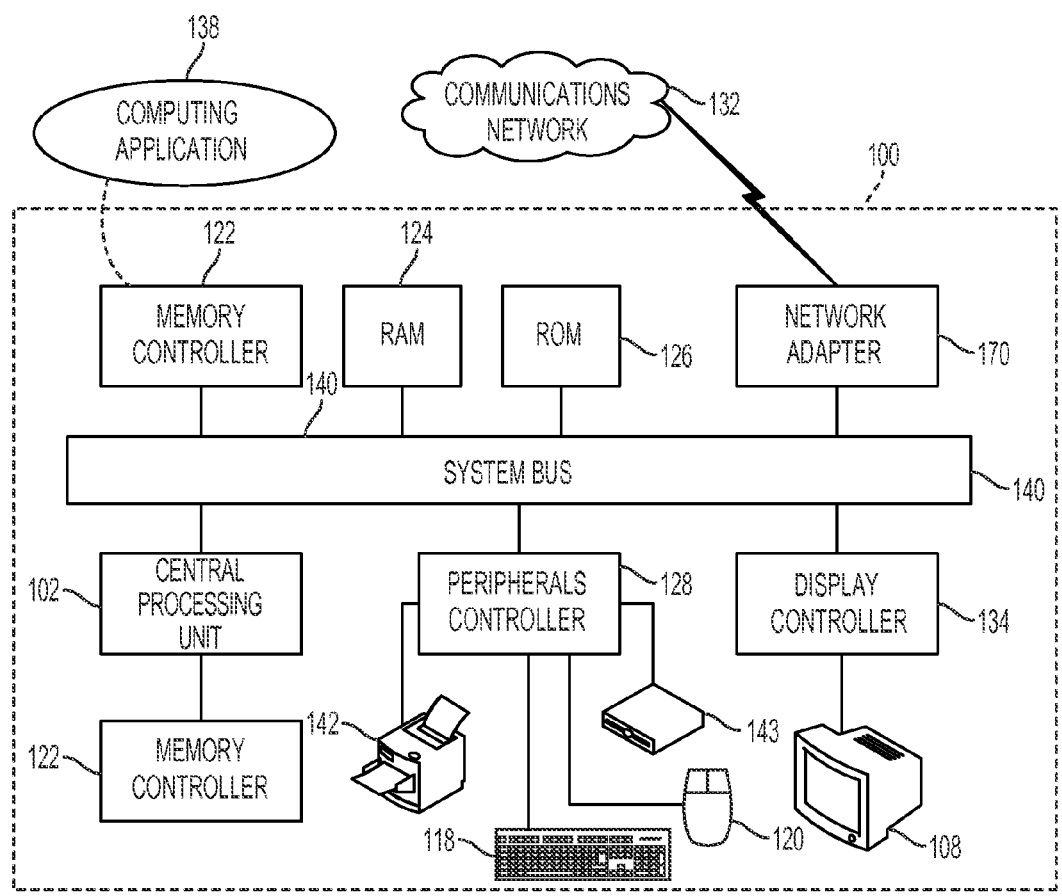
FIG. 1B is a block diagram of an exemplary computing environment through which use of physically intuitive complex working memory tasks improve cognition in accordance with the disclosure.

FIG. 1B depicts another exemplary computing system 100. The computing system 100 is capable of, or in at least some situations adaptable for, executing a variety of computing applications 138, including computing applications, a computing applet, a computing program, or other instructions for operating on computing system 100 to perform at least one function, operation, and/or procedure. Computing system 100 is controllable by computer readable storage media for tangibly storing computer readable instructions, which may be in the form of software. The computer readable storage media capable of, or in at least some situations adaptable to, tangibly store computer readable instructions can contain instructions for computing system 100 for storing and accessing the computer readable storage media to read the instructions stored thereon themselves. Such software may be executed within CPU 102 to cause the computing system 100 to perform desired functions. In many known computer servers, workstations and personal computers CPU 102 is implemented by micro-electronic chips CPUs called microprocessors. Optionally, a coprocessor, distinct from the main CPU 102, can be provided that performs additional functions or assists the CPU 102. The CPU 102 may be connected to co-processor through an interconnect. One common type of coprocessor is the floating-point coprocessor, also called a numeric or math coprocessor, which is designed to perform numeric calculations faster and better than the general-purpose CPU 102.

As will be appreciated by those skilled in the art, a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

In operation, the CPU 102 fetches, decodes, and executes instructions, and transfers information to and from other resources via the computer's main data-transfer path, system bus 140. Such a system bus connects the components in the computing system 100 and defines the medium for data exchange. Memory devices coupled to the system bus 140 include random access memory (RAM) 124 and read only memory (ROM) 126. Such memories include circuitry that allows information to be stored and retrieved. The ROMs 126 generally contain stored data that cannot be modified. Data stored in the RAM 124 can be read or changed by CPU 102 or other hardware devices. Access to the RAM 124 and/or ROM 126 may be controlled by memory controller 122. The memory controller 122 may provide an address translation function that translates virtual addresses into physical addresses as instructions are executed.

In addition, the computing system 100 can contain peripherals controller 128 responsible for communicating instructions from the CPU 102 to peripherals, such as, printer 142, keyboard 118, mouse 120, and data storage drive 143. Display 108, which is controlled by a display controller 163, is used to display visual output generated by the computing system 100. Such visual output may include text, graphics, animated graphics, and video. The display controller 134 includes electronic components required to generate a video signal that is sent to display 108. Further, the computing system 100 can contain network adaptor 136 which may be used to connect the computing system 100 to an external communications network 132.

II. Networks and Internet Protocol

As is well understood by those skilled in the art, the Internet is a worldwide network of computer networks. Today, the Internet is a public and self-sustaining network that is available to many millions of users. The Internet uses a set of communication protocols called TCP/IP (i.e., Transmission Control Protocol/Internet Protocol) to connect hosts. The Internet has a communications infrastructure known as the Internet backbone. Access to the Internet backbone is largely controlled by Internet Service Providers (ISPs) that resell access to corporations and individuals.

The Internet Protocol (IP) enables data to be sent from one device (e.g., a phone, a Personal Digital Assistant (PDA), a computer, etc.) to another device on a network. There are a variety of versions of IP today, including, e.g., IPv4, IPv6, etc. Other IPs are no doubt available and will continue to become available in the future, any of which can be used without departing from the scope of the invention. Each host device on the network has at least one IP address that is its own unique identifier and acts as a connectionless protocol. The connection between end points during a communication is not continuous. When a user sends or receives data or messages, the data or messages are divided into components known as packets. Every packet is treated as an independent unit of data and routed to its final destination—but not necessarily via the same path.

III. Wireless Networks

Wireless networks can incorporate a variety of types of mobile devices, such as, e.g., cellular and wireless telephones, PCs (personal computers), laptop computers, wearable computers, cordless phones, pagers, headsets, printers, PDAs, etc. For example, mobile devices may include digital systems to secure fast wireless transmissions of voice and/or data. Typical mobile devices include some or all of the following components: a transceiver (for example a transmitter and a receiver, including a single chip transceiver with an integrated transmitter, receiver and, if desired, other functions); an antenna; a processor; display; one or more audio transducers (for example, a speaker or a microphone as in devices for audio communications); electromagnetic data storage (such as ROM, RAM, digital data storage, etc., such as in devices where data processing is provided); memory; flash memory; and/or a full chip set or integrated circuit; interfaces (such as universal serial bus (USB), coder-decoder (CODEC), universal asynchronous receiver-transmitter (UART), phase-change memory (PCM), etc.). Other components can be provided without departing from the scope of the invention.

Wireless LANs (WLANs) in which a mobile user can connect to a local area network (LAN) through a wireless connection may be employed for wireless communications. Wireless communications can include communications that propagate via electromagnetic waves, such as light, infrared, radio, and microwave. There are a variety of WLAN standards that currently exist, such as Bluetooth®, IEEE 802.11, and the obsolete HomeRF.

By way of example, Bluetooth products may be used to provide links between mobile computers, mobile phones, portable handheld devices, personal digital assistants (PDAs), and other mobile devices and connectivity to the Internet. Bluetooth is a computing and telecommunications industry specification that details how mobile devices can easily interconnect with each other and with non-mobile devices using a short-range wireless connection. Bluetooth creates a digital wireless protocol to address end-user problems arising from the proliferation of various mobile devices that need to keep data synchronized and consistent from one device to another, thereby allowing equipment from different vendors to work seamlessly together.

An IEEE standard, IEEE 802.11, specifies technologies for wireless LANs and devices. Using 802.11, wireless networking may be accomplished with each single base station supporting several devices. In some examples, devices may come pre-equipped with wireless hardware or a user may install a separate piece of hardware, such as a card, that may include an antenna. By way of example, devices used in 802.11 typically include three notable elements, whether or not the device is an access point (AP), a mobile station (STA), a bridge, a personal computing memory card International Association (PCMCIA) card (or PC card) or another device: a radio transceiver; an antenna; and a MAC (Media Access Control) layer that controls packet flow between points in a network.

In addition, Multiple Interface Devices (MIDs) may be utilized in some wireless networks. MIDs may contain two independent network interfaces, such as a Bluetooth interface and an 802.11 interface, thus allowing the MID to participate on two separate networks as well as to interface with Bluetooth devices. The MID may have an IP address and a common IP (network) name associated with the IP address.

Wireless network devices may include, but are not limited to Bluetooth devices, WiMAX (Worldwide Interoperability for Microwave Access), Multiple Interface Devices (MIDs), 802.11x devices (IEEE 802.11 devices including, 802.11a, 802.11b and 802.11g devices), HomeRF (Home Radio Frequency) devices, Wi-Fi (Wireless Fidelity) devices, GPRS (General Packet Radio Service) devices, 3 G cellular devices, 2.5 G cellular devices, GSM (Global System for Mobile Communications) devices, EDGE (Enhanced Data for GSM Evolution) devices, TDMA type (Time Division Multiple Access) devices, or CDMA type (Code Division Multiple Access) devices, including CDMA2000. Each network device may contain addresses of varying types including but not limited to an IP address, a Bluetooth Device Address, a Bluetooth Common Name, a Bluetooth IP address, a Bluetooth IP Common Name, an 802.11 IP Address, an 802.11 IP common Name, or an IEEE MAC address.

Wireless networks can also involve methods and protocols found in, Mobile IP (Internet Protocol) systems, in PCS systems, and in other mobile network systems. With respect to Mobile IP, this involves a standard communications protocol created by the Internet Engineering Task Force (IETF). With Mobile IP, mobile device users can move across networks while maintaining their IP Address assigned once. See Request for Comments (RFC) 3344. NB: RFCs are formal documents of the Internet Engineering Task Force (IETF). Mobile IP enhances Internet Protocol (IP) and adds a mechanism to forward Internet traffic to mobile devices when connecting outside their home network. Mobile IP assigns each mobile node a home address on its home network and a care-of-address (CoA) that identifies the current location of the device within a network and its subnets. When a device is moved to a different network, it receives a new care-of address. A mobility agent on the home network can associate each home address with its care-of address. The mobile node can send the home agent a binding update each time it changes its care-of address using Internet Control Message Protocol (ICMP).

Figure 1C:
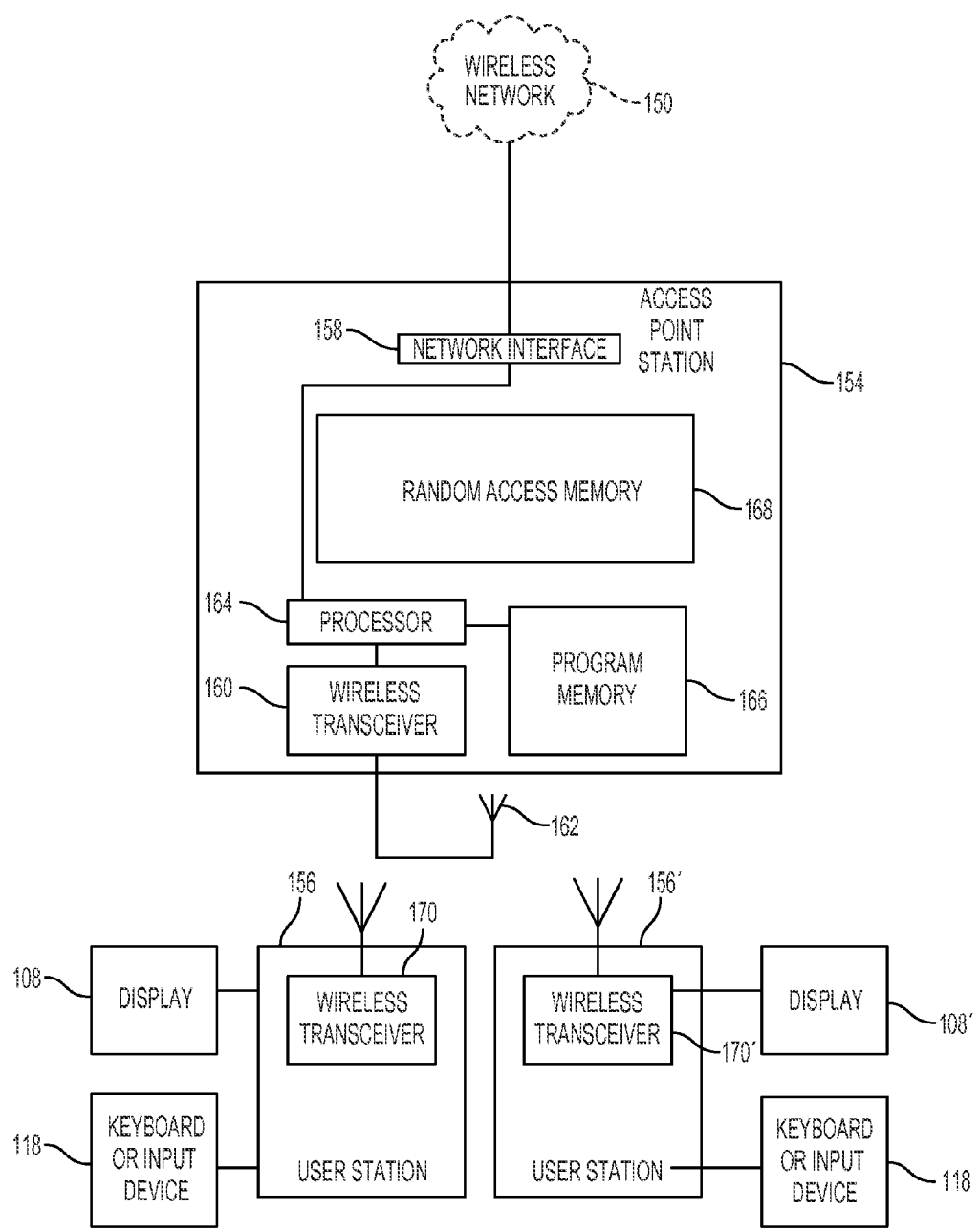
FIG. 1C is an illustrative architectural diagram showing some structure that can be employed by devices through which use of physically intuitive complex working memory tasks improve cognition in accordance with the disclosure.

FIG. 1C depicts components that can be employed in system configurations enabling the systems and technical effect of this disclosure, including wireless access points to which client devices communicate. In this regard, FIG. 1C shows a wireless network 150 connected to a wireless local area network (WLAN) 152. The WLAN 152 includes an access point (AP) 154 and a number of user stations 156, 156'. For example, the network 150 can include the Internet or a corporate data processing network. The access point 154 can be a wireless router, and the user stations 156, 156' can be portable computers, personal desk-top computers, PDAs, portable voice-over-IP telephones and/or other devices. The access point 154 has a network interface 158 linked to the network 150, and a wireless transceiver in communication with the user stations 156, 156'. For example, the wireless transceiver 160 can include an antenna 162 for radio or microwave frequency communication with the user stations 156, 156'. The access point 154 also has a processor 164, a program memory 166, and a random access memory 168. The user station 156 has a wireless transceiver 170 including an antenna 172 for communication with the access point station 154. In a similar fashion, the user station 156' has a wireless transceiver 170' and an antenna 172 for communication to the access point 154. By way of example, in some embodiments an authenticator could be employed within such an access point (AP) and/or a supplicant or peer could be employed within a mobile node or user station. Desktop 108 and key board 118 or input devices can also be provided with the user status.

IV. Access Via Browser

In at least some configurations, a user executes a browser to view digital content items and can connect to the front end server via a network, which is typically the Internet, but can also be any network, including but not limited to any combination of a LAN, a MAN, a WAN, a mobile, wired or wireless network, a private network, or a virtual private network. As will be understood a very large numbers (e.g., millions) of users are supported and can be in communication with the website at any time. The user may include a variety of different computing devices. Examples of user devices include, but are not limited to, personal computers, digital assistants, personal digital assistants, cellular phones, mobile phones, smart phones or laptop computers.

The browser can include any application that allows users to access web pages on the World Wide Web. Suitable applications include, but are not limited to, Microsoft Internet Explorer®, Netscape Navigator®, Mozilla® Firefox, Apple® Safari or any application capable of or adaptable to allowing access to web pages on the World Wide Web. The browser can also include a video player (e.g., Flash™ from Adobe Systems, Inc.), or any other player adapted for the video file formats used in the video hosting website. Alternatively, videos can be accessed by a standalone program separate from the browser. A user can access a video from the website by, for example, browsing a catalog of digital content, conducting searches on keywords, reviewing aggregate lists from other users or the system administrator (e.g., collections of videos forming channels), or viewing digital content associated with particular user groups (e.g., communities).

V. Computer Network Environment

Figure 2:
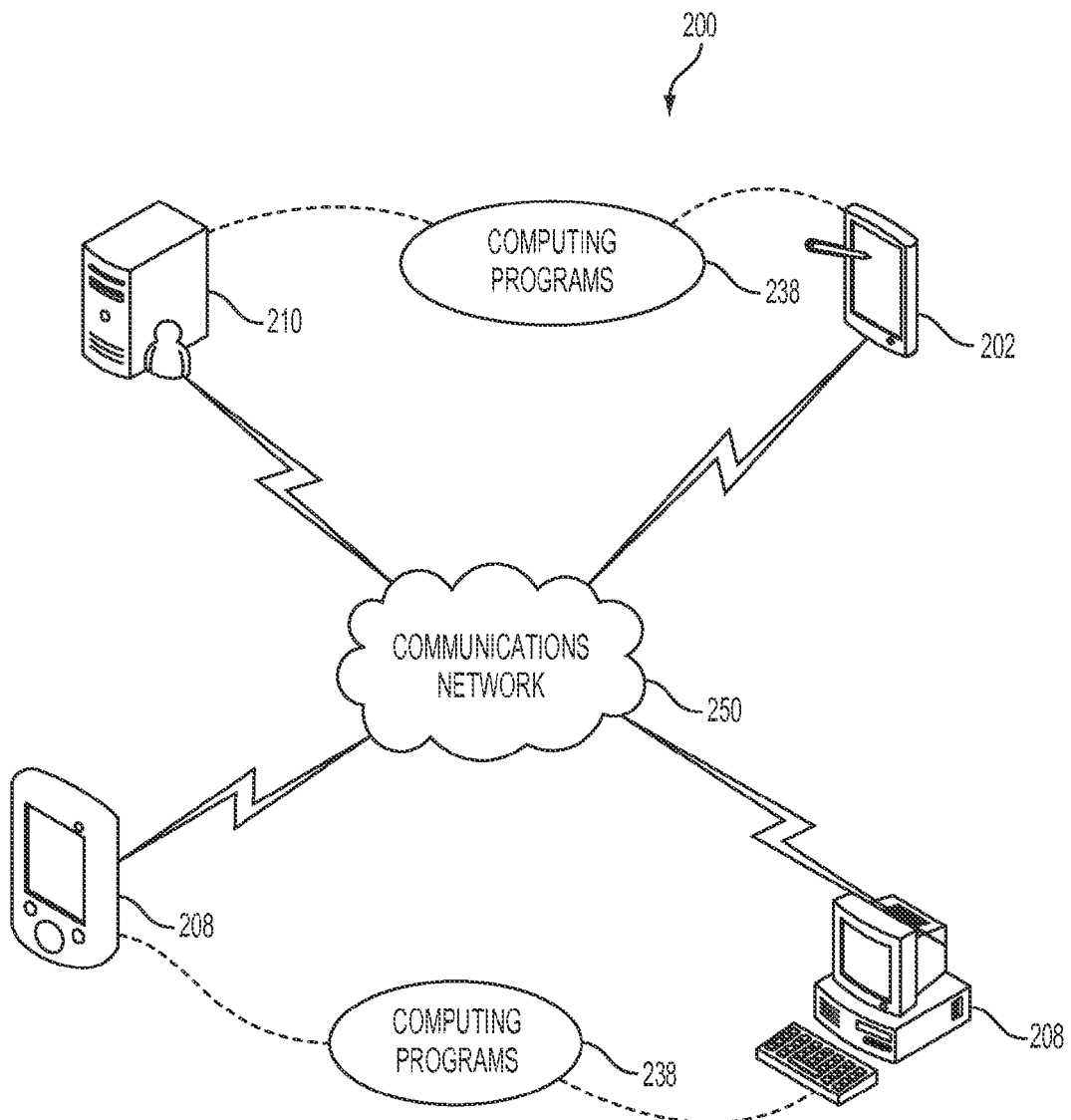
FIG. 2 is a block diagram showing the cooperation of exemplary components of a system suitable for use in a system in which use of physically intuitive complex working memory tasks improve cognition in accordance with the disclosure.

Computing system 100, described above, can be deployed as part of a computer network used to achieve the desired technical effect and transformation. In general, the above description for computing environments applies to both server computers and client computers deployed in a network environment. FIG. 2 illustrates an exemplary illustrative networked computing environment 200, with a server in communication with client computers via a communications network 250. As shown in FIG. 2, server 210 may be interconnected via a communications network 250 (which may be either of, or a combination of a fixed-wire or wireless LAN, WAN, intranet, extranet, peer-to-peer network, virtual private network, the Internet, or other communications network) with a number of client computing environments such as tablet personal computer 202, smart phone 204, personal computer 202, and personal digital assistant 208. In a network environment in which the communications network 250 is the Internet, for example, server 210 can be dedicated computing environment servers operable to process and communicate data to and from client computing environments via any of a number of known protocols, such as, hypertext transfer protocol (HTTP), file transfer protocol (FTP), simple object access protocol (SOAP), or wireless application protocol (WAP). Other wireless protocols can be used without departing from the scope of the disclosure, including, for example Wireless Markup Language (WML), DoCoMo i-mode (used, for example, in Japan) and XHTML Basic. Additionally, networked computing environment 200 can utilize various data security protocols such as secured socket layer (SSL) or pretty good privacy (PGP). Each client computing environment can be equipped with operating system 238 operable to support one or more computing applications, such as a web browser (not shown), or other graphical user interface (not shown), or a mobile desktop environment (not shown) to gain access to server computing environment 200.

In operation, a user (not shown) may interact with a computing application running on a client computing environment to obtain desired data and/or computing applications. The data and/or computing applications may be stored on server computing environment 200 and communicated to cooperating users through client computing environments over exemplary communications network 250. The computing applications, described in more detail below, are used to achieve the desired technical effect and transformation set forth. A participating user may request access to specific data and applications housed in whole or in part on server computing environment 200. These data may be communicated between client computing environments and server computing environments for processing and storage. Server computing environment 200 may host computing applications, processes and applets for the generation, authentication, encryption, and communication data and applications and may cooperate with other server computing environments (not shown), third party service providers (not shown), network attached storage (NAS) and storage area networks (SAN) to realize application/data transactions.

Figure 3A:
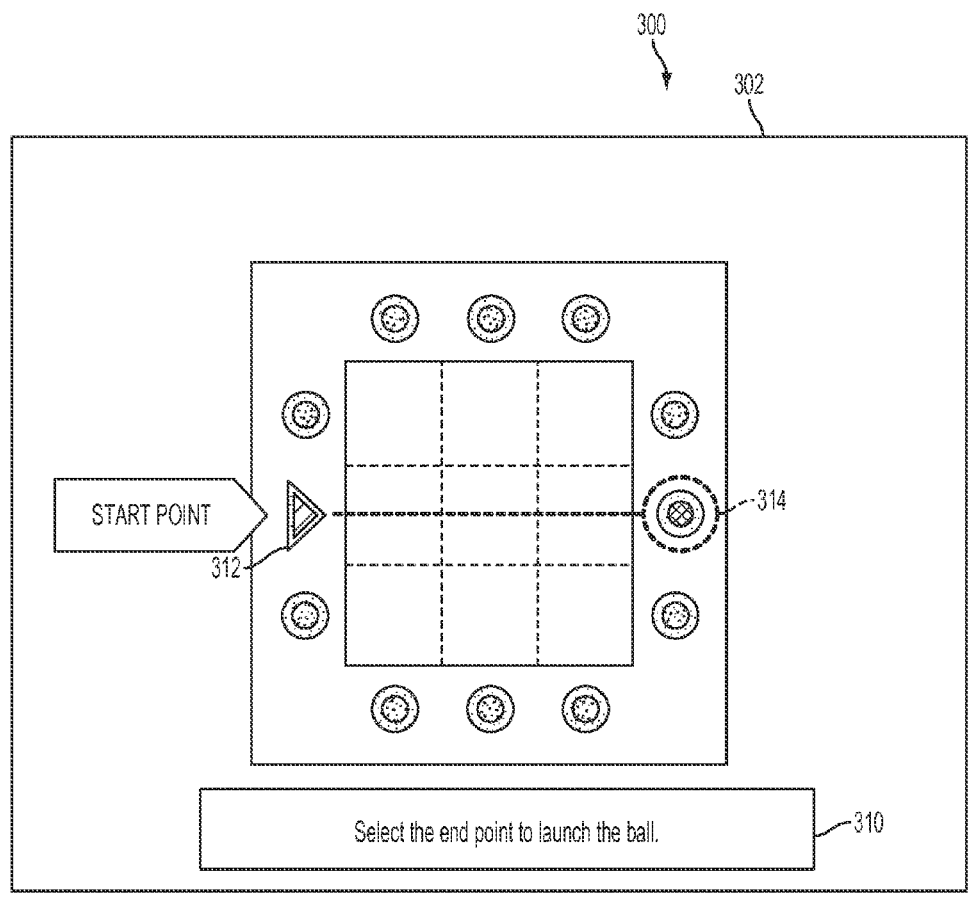
FIG. 3A depicts a screen shot of a portion of a tutorial explaining a main task for a game in accordance with the disclosure.

VII. Software Programs Implementable in the Computing and Network Environments to Achieve a Desired Technical Effect or Transformation FIG. 3A depicts a screen shot 300 of a board 302 and a portion of a tutorial explaining a main task for a game. An instruction 310 is provided on the screen, for example "Select the end point to launch the ball." A start point 312 appears in a first location on the board 302, and an end point 314 is in a second location different from the first on the board 302. As depicted in this screen shot, for example, the start point 312 is on the left side of the screen and the end point 314 is on the right side of the screen.

Figure 3B:
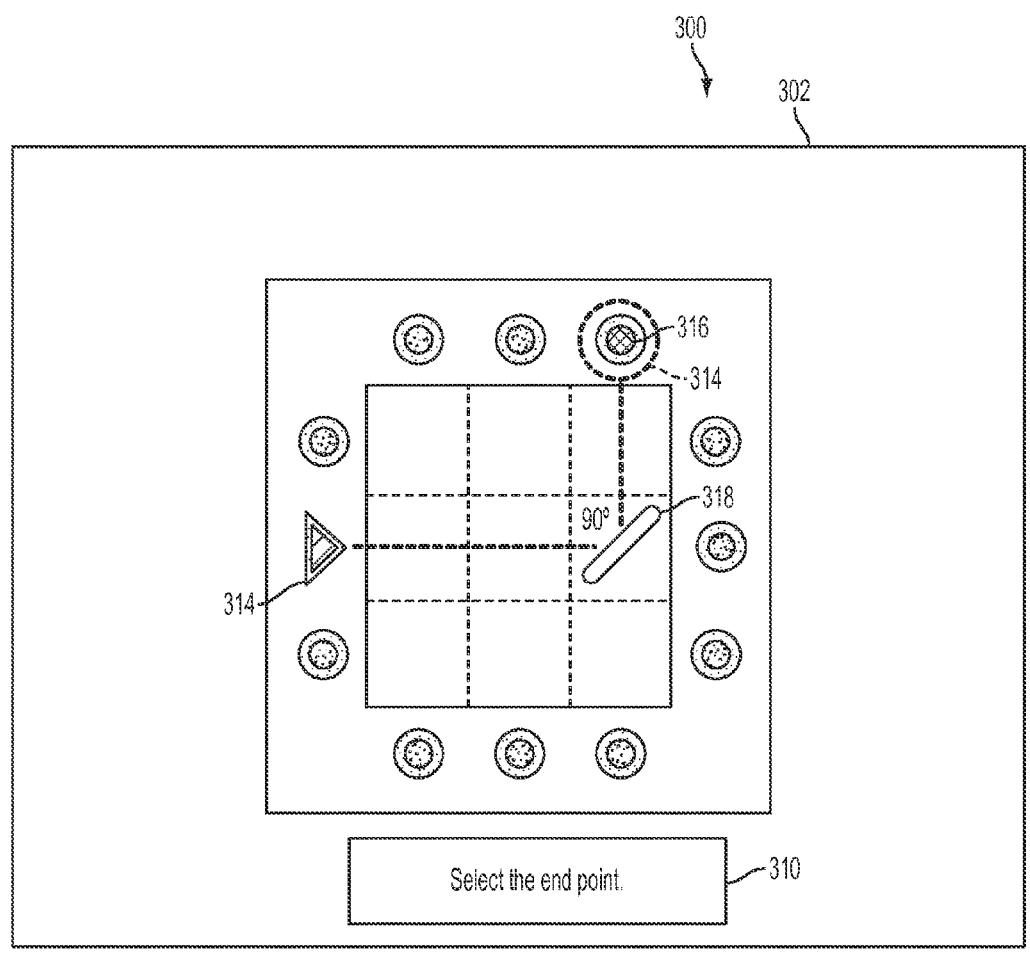
FIG. 3B depicts a screen shot of a portion of a tutorial prompting a user to select an endpoint and providing a description of the way in which a pinball bounces off a bumper in accordance with the disclosure.

FIG. 3B depicts a screen shot 300 of a portion of a tutorial prompting a user to select an endpoint and providing a description of the way in which a pinball 316 bounces off a graphical element having at least one linear face such as a bumper 318. Thus, for example, the start point 312 is depicted on the left side of the board 302, with a bumper 318 on the right side of the board 302 directly across from the start point. The bumper 318 is depicted as a linear segment having a length sufficient to engage a surface of the pinball 316 such that the pinball 316 will strike the bumper and be deflected in a new direction. In this depiction, the bumper 318 is positioned horizontally across from the start point 312 and is angled at 45° angle from the horizontal such that when the pinball 316 hits the surface of the bumper 318 it travels in a direction perpendicular to it's first direction of travel (90° from horizontal).

Figure 4:
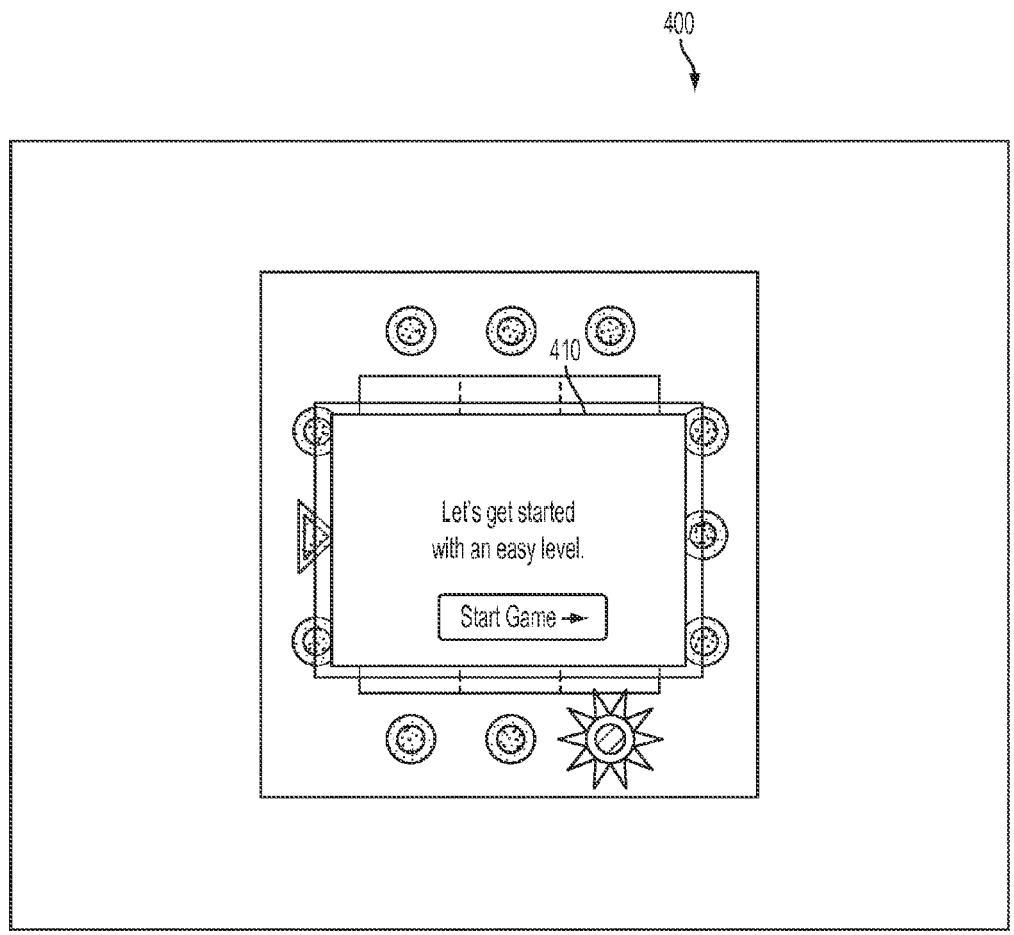
FIG. 4 depicts a screen shot indicating completion of the tutorial, including a prompt to begin a game in accordance with the disclosure.
Figure 5:
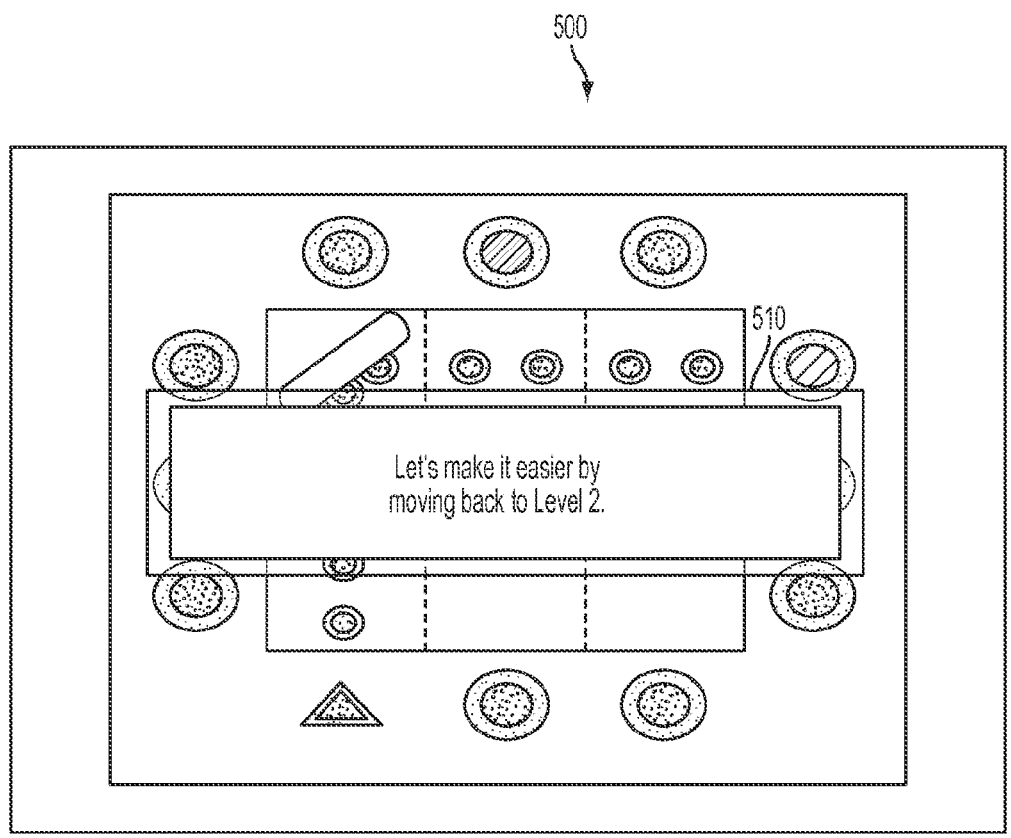
FIG. 5 depicts a screen shot alerting a user that the level of game play has been decreased in accordance with the disclosure.
Figure 6:
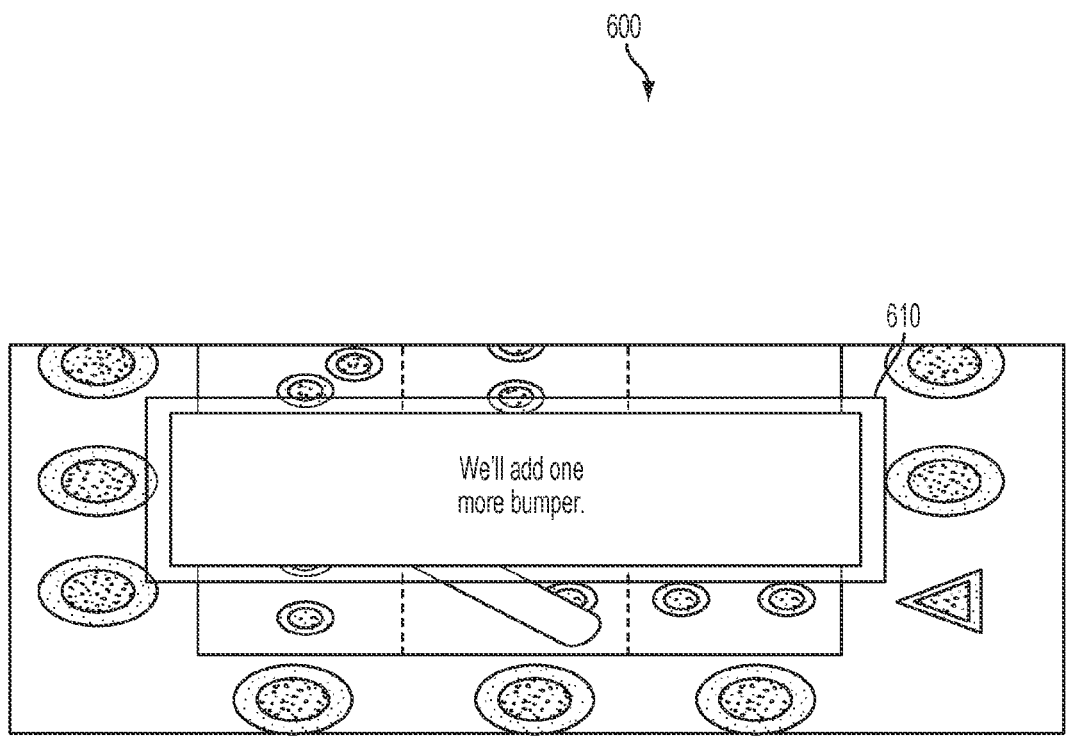
FIG. 6 depicts a screen shot alerting the user that an increase in difficulty will be added to the game in accordance with the disclosure.
Figure 7:
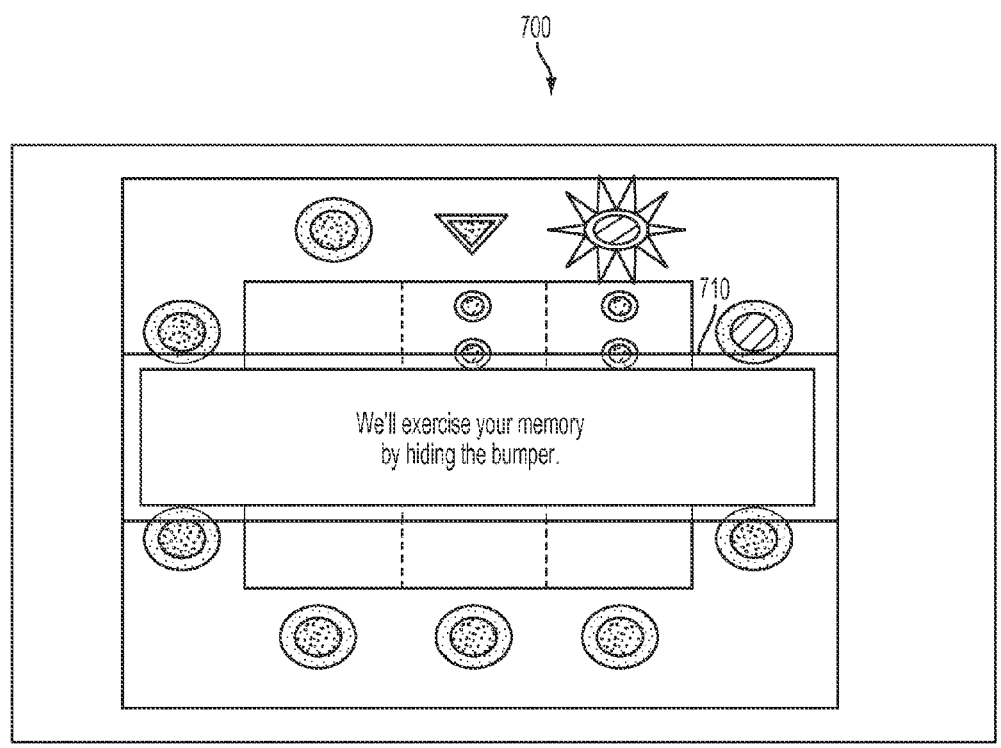
FIG. 7 depicts a screen shot alerting the user that bumpers will be hidden in order to exercise the user's working memory in accordance with the disclosure.

FIG. 4 depicts a screen shot 400 indicating completion of the tutorial, including a prompt 410 to begin a game. FIG. 5 depicts a screen shot 500 with an instruction 510 alerting a user that the level of game play has been decreased. FIG. 6 depicts a screen shot 600 with an instruction 610 alerting the user that an increase in difficulty will be added to the game. FIG. 7 depicts a screen shot 700 with an instruction 710 alerting the user that bumpers will be hidden in order to exercise the user's working memory.

Figure 8:
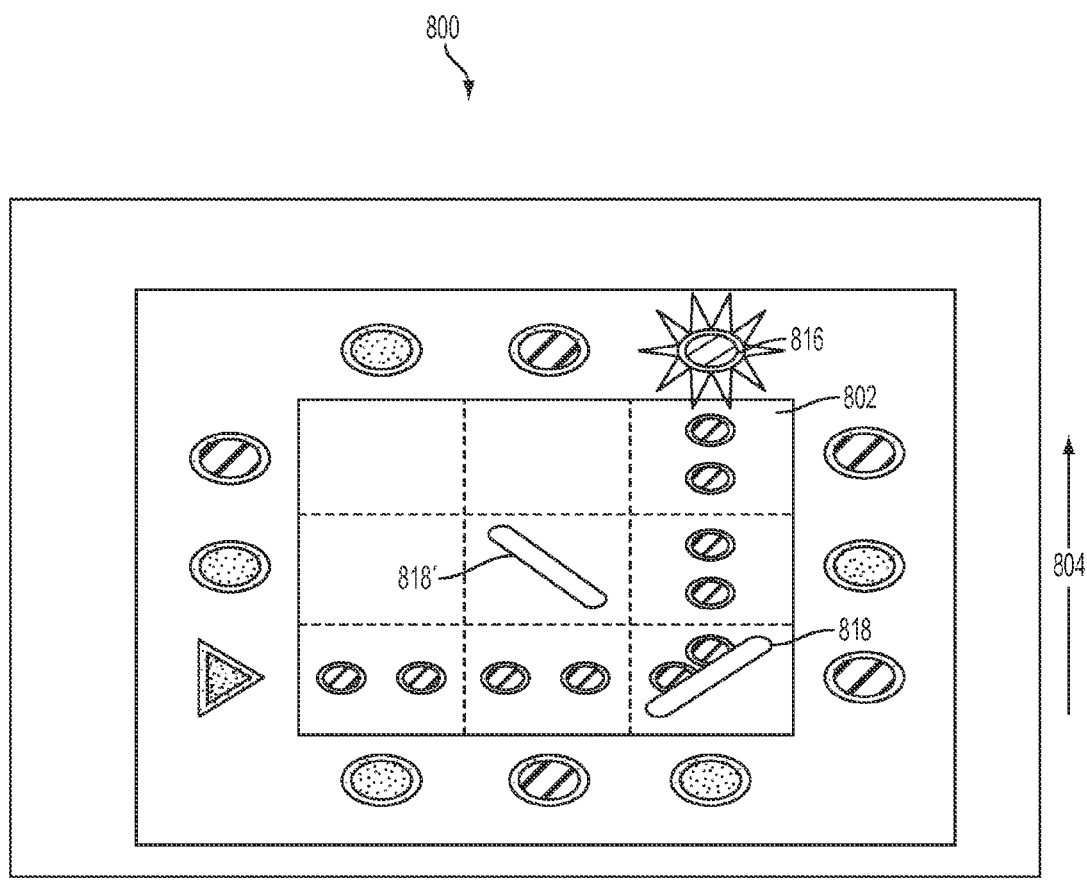
FIG. 8 depicts a screen shot illustrating a decoy bumper placed in the board configuration which does not interfere with the route of the pinball in accordance with the disclosure.

FIG. 8 depicts a screen shot 800 illustrating a bumper 818 and a decoy bumper 818' placed in the board 802 configuration which does not interfere with the route 804 of the pinball 816.

Figure 9:
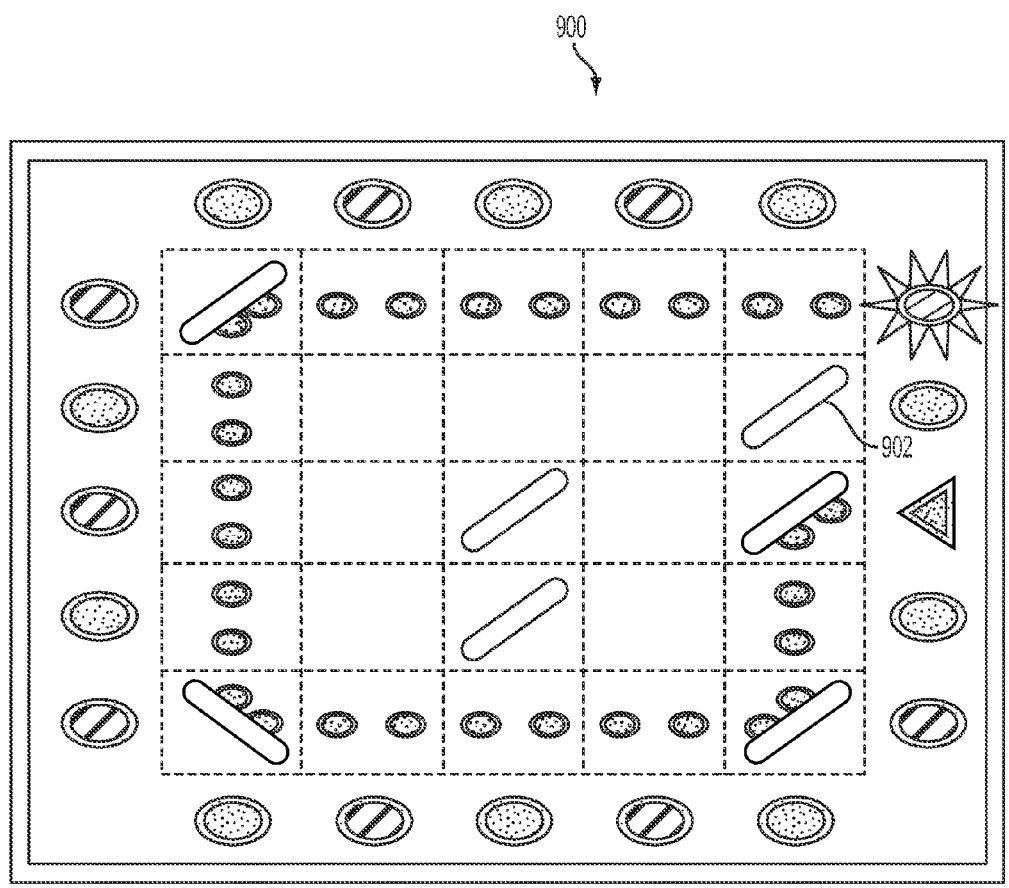
FIG. 9 depicts a screen shot illustrating an example of a complex, dynamic board configuration containing an exemplar 5×5 grid and 3 decoy bumpers in accordance with the disclosure.

FIG. 9 depicts a screen shot illustrating an example of a complex, dynamic board 902 configuration containing an exemplar 5×5 grid and 3 decoy bumpers.

Figure 10:
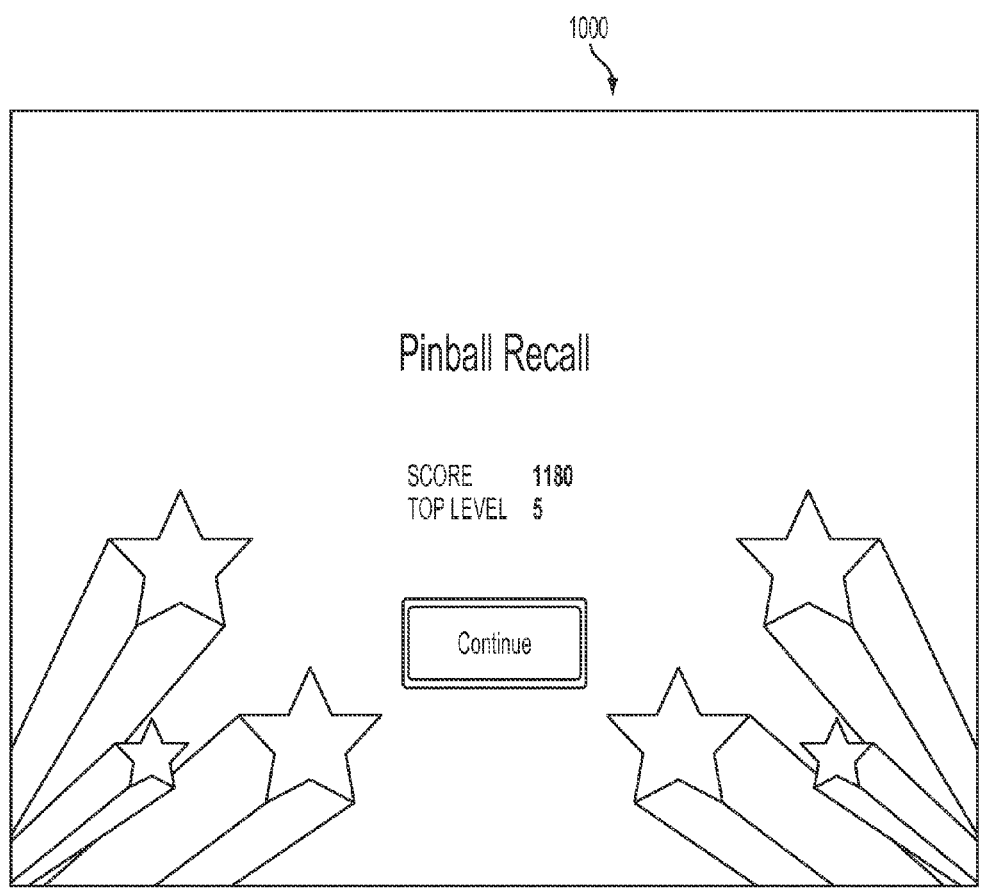
FIG. 10 depicts a screen shot with a final result containing a user score and highest level achieved in accordance with the disclosure.

FIG. 10 depicts a screen shot 1000 with a final result containing a user score and highest level achieved.

The object of this exercise is for a user to successfully get the pinball from the starting point to the ending point by bouncing the pinball off the bumpers positioned on the board. Initially, all bumpers are presented on the board such that the bumpers are visible to the user for a brief period of time. Then, in most levels, the bumpers disappear and are no longer visible by the user. After the bumpers disappear, the user is shown the ball's starting point and must determine, based on the positioning of the now-invisible bumpers, where the ball will end up. This requires the user to recall the position that the bumpers had occupied. The ball always travels outward perpendicularly from the wall where it is launched until it hits a bumper. The ball ricochets off the bumpers according to the rule, "the angle of incidence equals the angle of deflection." In a current implementation, all bumpers are angled at 45 degrees, but, as will be appreciated by those skilled in the art, this could be altered in other implementations. For example, all bumpers could be positioned at an angle other than 45 degrees, or bumpers could be positioned at a plurality of angles.

If the correct end point is selected, the user is rewarded for a correct trial. If the incorrect point is chosen, the user receives the incorrect trial feedback, and is shown the correct path. This exercise requires the user to recall the location and orientation of all the bumpers, while calculating a route through grid. This exercises working memory systems in a domain general way, in a form that is physically intuitive and engaging.

The user is introduced to the training exercise via a short interactive tutorial describing the gameplay elements, (FIGS. 3A-B). The tutorial prompts the user to complete a series of simple game configurations with guided messages and prompts. Gameplay features such as the angle at which the pinball bounces off of each bumper are explained with animations and helpful text, (FIG. 3B). Once the tutorial is completed, the user is prompted to play the game at the first level, (FIG. 4).

The main gameplay flow is based on varying levels of difficulty. As the user progresses up through each level, the difficulty is increased. If two incorrect answers are selected in a row, the user is moved down a level and the difficulty is decreased, (FIG. 5). Once two correct answers are selected in a row, the user is moved up a level and the difficulty is increased until a total of 15 trials are completed—this is the current best mode, but other game lengths (i.e., number of trials) and methods of moving up and down in difficulty (e.g., one correct or incorrect to change level, or a Bayesian adaptive algorithm predicting the optimal level) could be used as well.

On subsequent plays of the game, the user starts just below their previous level. This allows the user to regain familiarity with the training task and helps build confidence. In some configurations, the user starts at a subsequent start level that can be based on, for example, the previous level as well as the length of time that has passed since a user has last played.

Difficulty is controllable by adjusting one or more of the following variables:
Board size
  An initial level starts at a 3×3 grid and grows to, for example, 6×6
Number of bumpers on the board, (FIG. 6)
Visibility of bumpers or decoy bumpers
  At later levels, bumpers and/or decoy bumpers are shown and then hidden, (FIG. 7)
  The amount of time the bumpers or decoy bumpers are visible
  The number of bumpers and/or decoy bumpers that are visible (e.g., a subset of bumpers and/or decoy bumpers can be made invisible)
Number of decoy bumpers
  In order to mitigate memorization of board configurations, decoy bumpers are added which are never activated during the trial, (FIG. 8)
Size (e.g., length) of bumpers and/or decoy bumpers
Shape of bumpers and/or decoy bumpers
Angle of bumpers and/or decoy bumpers
  All bumpers and/or decoy bumpers angled at a single angle (e.g., 45 degrees)
  Bumpers and/or decoy bumpers angled as a plurality of angles The core gameplay mechanic is the selection of the final position for the pinball based on a starting location and a series of bumpers that make up a board configuration. This configuration is determined by the current level of difficulty and has been designed to provide a smooth transition between levels.

As will be appreciated by those skilled in the art, implementation can also vary depending on the platform for delivery. For example, the grid configuration may be adapted to the screen size of the electronic device and the nature of the input mode. Thus, in one configuration a grid of 3×3 which uses a mouse click as input could be the configuration in a computer while a grid of 5×7 which relies on a touch screen interface for input might be used for a mobile device or tablet.

The process of generating a dynamic board configuration begins with the selection of the target board size and the number of bumpers and decoys from within a range based on the difficulty of the current level. In the current best mode implementation, these ranges have been hardcoded into the game based on user testing and are updated periodically from data gathered across a large user-base of active players (TABLE 1).

Once the board size, number of bumpers, and number of decoys have been determined, bumpers are randomly placed on the board to generate a route to an end location. These bumpers are then oriented in such a way as to create a valid surface on which the pinball will bounce and continue along the generated path. Once the route is determined, decoy bumpers are placed on grid elements that do not lie along the route. If the randomly chosen route does not allow for the placement of the selected number of decoy bumpers, a new route is generated until a valid route is found. In this way a complete board configuration is generated. Since routes are dynamically determined, there are a vast number of possible routes and therefore unique trials (FIG. 9).

After a predetermined number of trials (e.g., fifteen trials), the user's game is completed and they are shown a results screen on which their score is displayed alongside the highest level of difficulty achieved (FIG. 10).

TABLE 1

| Level | Board Size | Number of Bumpers | Decoy Range |
|---|---|---|---|
| 1 | 3 × 3 | 1 | 0-0 |
| 2 | 3 × 3 | 2 | 0-1 |
| 3 | 3 × 3 | 1 | 0-0 |
| 4 | 3 × 3 | 2 | 0-1 |
| 5 | 4 × 4 | 3 | 1-2 |
| 6 | 4 × 4 | 4 | 1-3 |
| 7 | 5 × 5 | 4 | 1-2 |
| 8 | 5 × 5 | 5 | 2-3 |
| 9 | 5 × 5 | 6 | 3-4 |
| 10 | 5 × 5 | 7 | 4-5 |
| 11 | 5 × 5 | 7 | 3-4 |
| 12 | 5 × 5 | 8 | 3-6 |
| 13 | 6 × 6 | 8 | 2-5 |
| 14 | 6 × 6 | 9 | 3-5 |
| 15 | 6 × 6 | 9 | 2-5 |
| 16 | 6 × 6 | 10 | 3-6 |
| 17 | 6 × 6 | 11 | 4-7 |
| 18 | 6 × 6 | 12 | 4-8 |
| 19 | 6 × 6 | 13 | 5-8 |
| 20 | 6 × 6 | 14 | 5-9 |
| 21 | 6 × 6 | 15 | 6-9 |
| 22 | 6 × 6 | 16 | 6-10 |

Figure 11:
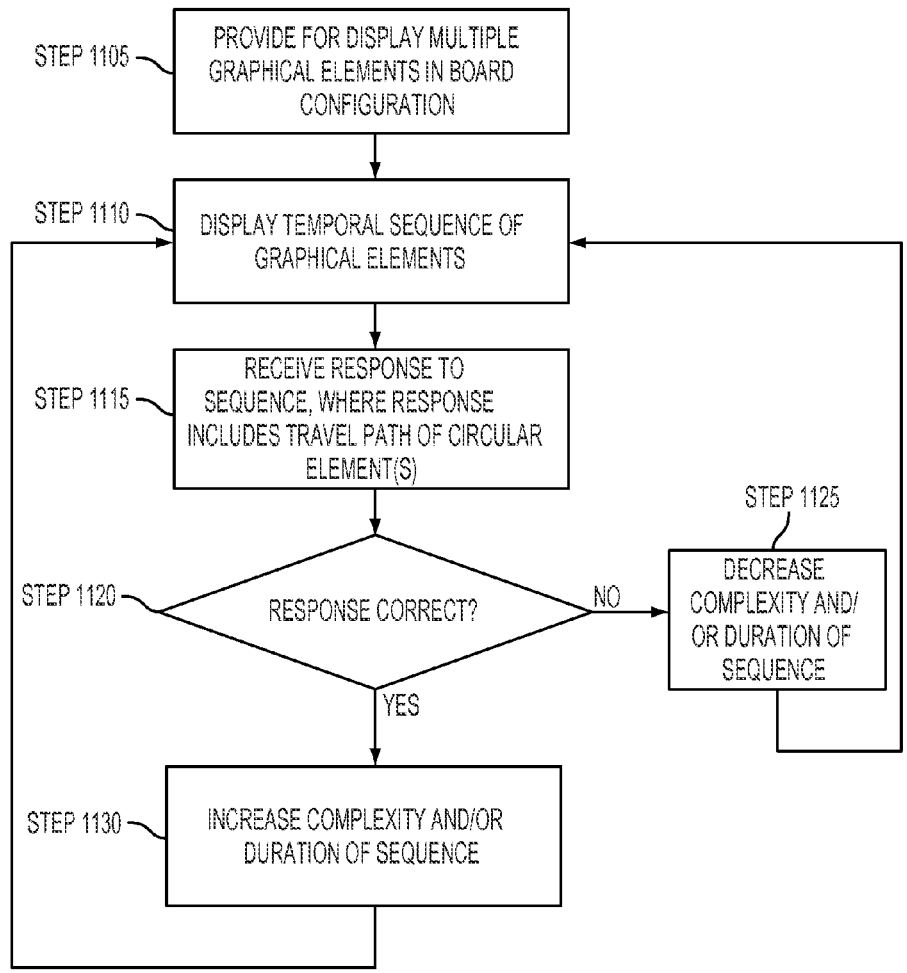
FIG. 11 depicts a flow chart of steps performed by a computing device in accordance with the disclosure.

FIG. 11 is a flowchart illustrating an embodiment of steps performed by a computing device to enhance cognition of a participant. The computing device provides for display multiple graphical elements in a board configuration (Step 1105). A temporal sequence of graphical elements is displayed (Step 1110), where the graphical elements include circular elements (e.g., pinballs), linear elements (e.g., bumpers), and/or decoy linear elements (e.g., decoy bumpers). The participant responds to the presented sequence and the computing device receives the response (Step 1115). The response includes an indication of a travel path for the one or more circular elements from a start point to an end point which travel path involves the circular elements engaging the linear elements and not engaging the decoy linear elements. The computing device then determines if the response is correct (Step 1120). If the response is incorrect, in one embodiment the complexity and/or the duration of the sequence is decreased (Step 1125). If the response is correct, in one embodiment the complexity and/or the duration of the sequence is increased (Step 1130). Steps 1110-1130 can then be repeated in an iterative manner to improve the cognition of the participant. In one embodiment, the board is a grid. The size of the grid can be adjusted to adjust complexity.

Figure 12:
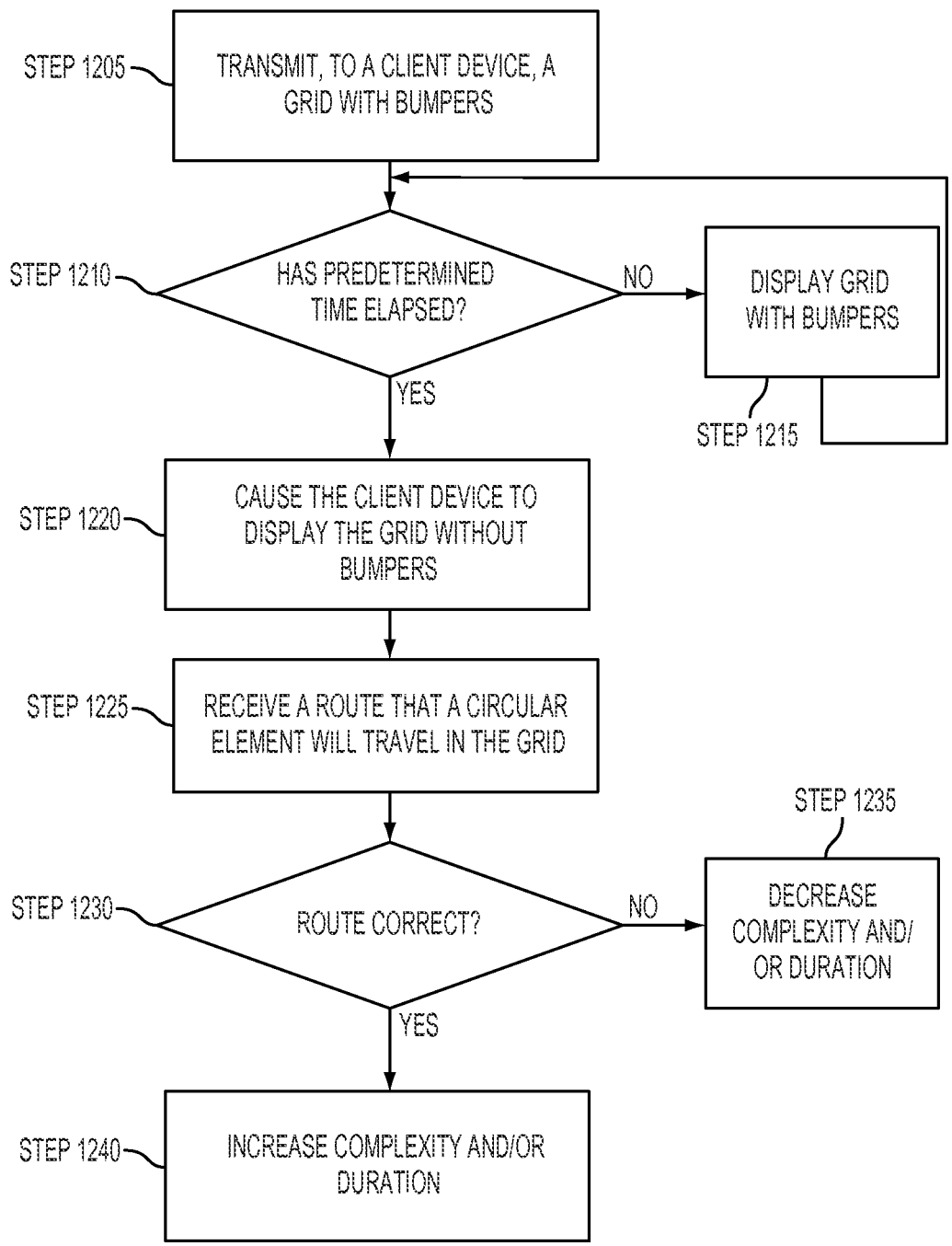
FIG. 12 depicts another flow chart of steps performed by a computing device in accordance with the disclosure.

FIG. 12 is another flowchart illustrating an embodiment of steps performed by a computing device to enhance cognition of a participant or user of a client device. A computing device transmits, to the client device for display for a predetermined amount of time, a grid with bumpers placed in different positions throughout the grid (Step 1205). The computing device determines if the predetermined amount of time has elapsed (Step 1210). If not, the grid with bumpers continues to be displayed (Step 1215). If so, the computing device causes the client device to display the grid without the bumpers (Step 1220). The computing device then receives, from the user, a route that a circular element will travel after being released from a designated starting position (Step 1225). The computing device determines if the received route is correct (Step 1230). In one embodiment, the complexity of the grid and/or the duration of the display of the grid with bumpers is adjusted based on if the route is correct (Steps 1235 or 1240). In one embodiment, the complexity is adjusted by adjusting the size of the grid.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for enhancing cognition of a participant, the method comprising:
    providing, via a computing device, multiple graphical elements in a board configuration, wherein the multiple graphical elements are available for visual presentation to the participant;
    visually presenting a temporal sequence of a plurality of graphical elements, including displaying, via a user interface display device, each graphical element at a respective location in a visual field, wherein the plurality of graphical elements includes two or more of each of one or more circular elements, one or more linear elements, and one or more decoy linear elements;
    requiring the participant to respond, via the user interface display device, to the presented temporal sequence, including indicating a travel path for the one or more circular elements from a start point to an end point, by selecting the correct end point on the board configuration, which travel path involves the circular elements engaging the linear elements and not engaging the decoy linear elements;
    determining whether the participant responded correctly by selecting the end point;
    modifying at least one of a duration of the visually presenting or complexity of the visually presenting based on the determining; and
    repeating the visually presenting, the requiring, the determining, and the modifying one or more times in an iterative manner to improve the cognition of the participant.

2. The method of claim 1, wherein the one or more circular elements comprises one or more pinballs.

3. The method of claim 1, wherein the one or more linear elements comprises one or more bumpers.

4. The method of claim 1, wherein the one or more decoy linear elements comprises one or more decoy bumpers.

5. The method of claim 1, wherein the board configuration further comprises a grid.

6. The method of claim 5, further comprising adjusting a size of the grid to provide additional mechanism for adjusting complexity.

7. A method for enhancing cognition of a user of a client device comprising:
    transmitting, via a computing device to the client device for display for a predetermined amount of time, a grid with bumpers placed in different positions throughout the grid;
    after the predetermined amount of time has elapsed, causing the client device to display the grid without the bumpers;
    after the display of the grid without the bumpers, receiving, by the computing device from the client device, a route that a circular element will travel in the grid after being released from a designated starting position, through the selection by the user of a correct exit position on the grid; and
    determining, via the computing device, whether the user selected the correct exit position.

8. The method of claim 7, further comprising adjusting a size of the grid to provide an additional mechanism for adjusting complexity.

9. A computing device for enhancing cognition of a participant, the computing device comprising:
    a processor;
    a storage medium for tangibly storing thereon program logic for execution by the processor, the program logic, when executed by the processor, performing a method comprising:
        providing multiple graphical elements in a board configuration, wherein the multiple graphical elements are available for visual presentation to the participant;
        visually presenting on a user interface display device a temporal sequence of a plurality of graphical elements, including displaying each graphical element at a respective location in a visual field, wherein the plurality of graphical elements includes two or more of each of one or more circular elements, one or more linear elements, and one or more decoy linear elements;
        requiring the participant to respond to the presented temporal sequence, including indicating a travel path for the one or more circular elements from a start point to an end point, by selecting the correct end point on the board configuration, which travel path involves the circular elements engaging the linear elements and not engaging the decoy linear elements;
        determining whether the participant responded correctly, by selecting the correct end point;
        modifying at least one of a duration of the visually presenting or complexity of the visually presenting based on the determining; and
        repeating the visually presenting, the requiring, the determining, and the modifying one or more times in an iterative manner to improve the cognition of the participant.

10. The computing device of claim 9, wherein the one or more circular elements comprises one or more pinballs.

11. The computing device of claim 9, wherein the one or more linear elements comprises one or more bumpers.

12. The computing device of claim 9, wherein the one or more decoy linear elements comprises one or more decoy bumpers.

13. The computing device of claim 9, wherein the board configuration further comprises a grid.

14. The computing device of claim 13, the method further comprising adjusting a size of the grid to provide an additional mechanism for adjusting complexity.

15. A non-transitory computer readable storage medium tangibly storing computer program instructions that, when executed by a computing device, cause the computing device to perform a method comprising:
- providing multiple graphical elements in a board configuration, wherein the multiple graphical elements are available for visual presentation to the participant;
- visually presenting a temporal sequence of a plurality of graphical elements, including displaying each graphical element at a respective location in a visual field, wherein the plurality of graphical elements includes two or more of each of one or more circular elements, one or more linear elements, and one or more decoy linear elements;
- requiring the participant to respond, via a user interface, to the presented temporal sequence, including indicating a travel path for the one or more circular elements from a start point to an end point, by selecting a correct end point, which travel path involves the circular elements engaging the linear elements and not engaging the decoy linear elements;
- determining whether the participant responded correctly by selecting the correct end point;
- modifying at least one of a duration of the visually presenting or complexity of the visually presenting based on the determining; and
- repeating the visually presenting, the requiring, the determining, and the modifying one or more times in an iterative manner to improve the cognition of the participant.

16. The non-transitory computer readable storage medium of claim 15, wherein the one or more circular elements comprises one or more pinballs.

17. The non-transitory computer readable storage medium of claim 15, wherein the one or more linear elements comprises one or more bumpers.

18. The non-transitory computer readable storage medium of claim 15, wherein the one or more decoy linear elements comprises one or more decoy bumpers.

19. The non-transitory computer readable storage medium of claim 15, wherein the board configuration further comprises a grid.

20. The non-transitory computer readable storage medium of claim 19, the method further comprising adjusting a size of the grid to provide additional mechanism for adjusting complexity.

* * * * *